United States Patent [19]

Schoenholz et al.

[11] 3,965,905

[45] June 29, 1976

[54] CATAMENIAL TAMPON

[75] Inventors: Daniel Schoenholz, Basking Ridge; Myron S. Weinberg, Livington, both of N.J.

[73] Assignee: Warner-Lambert Company, Morris Plains, N.J.

[22] Filed: Sept. 24, 1975

[21] Appl. No.: 616,231

Related U.S. Application Data

[63] Continuation of Ser. No. 271,453, July 13, 1972, abandoned.

[52] U.S. Cl. .............................. 128/285; 128/130; 128/270
[51] Int. Cl.² ............................................ A61F 13/20
[58] Field of Search ........... 128/130, 263, 270, 285, 128/296

[56] References Cited

UNITED STATES PATENTS

| 2,831,485 | 4/1958 | Haeseler | 128/285 |
| 2,858,831 | 11/1958 | Graham, Jr. | 128/285 |
| 3,084,689 | 4/1963 | Maro et al. | 128/270 |
| 3,306,295 | 2/1967 | Penksa | 128/285 |
| 3,811,445 | 5/1974 | Dostal | 128/285 |

Primary Examiner—Aldrich F. Medbery
Attorney, Agent, or Firm—Albert H. Graddis; Frank S. Chow; George M. Yahwak

[57] ABSTRACT

The present invention relates to an improved intravaginal catamenial tampon which is comprised of a plurality of individual small absorbent masses attached at intervals along a string.

6 Claims, 4 Drawing Figures

U.S. Patent June 29, 1976 3,965,905
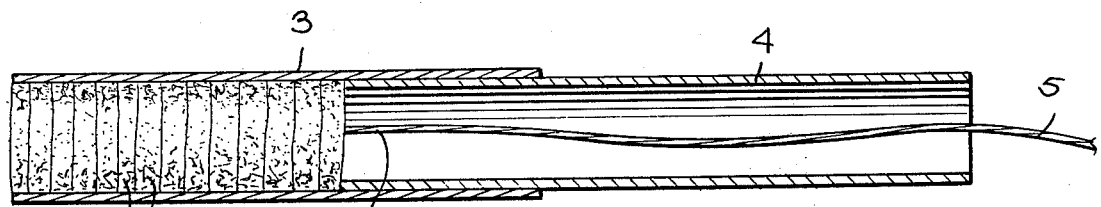
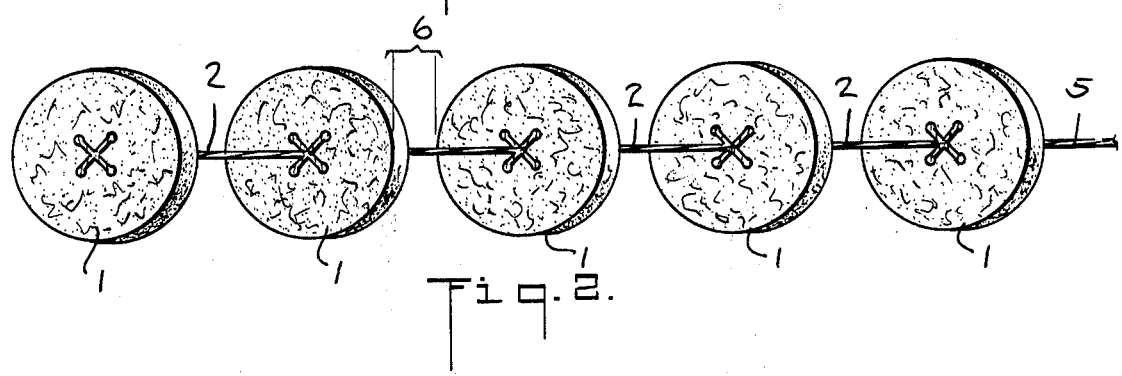
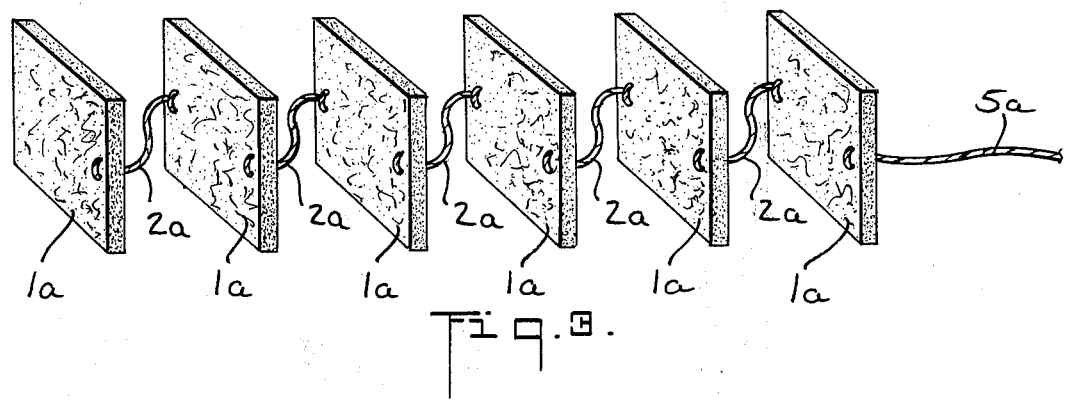
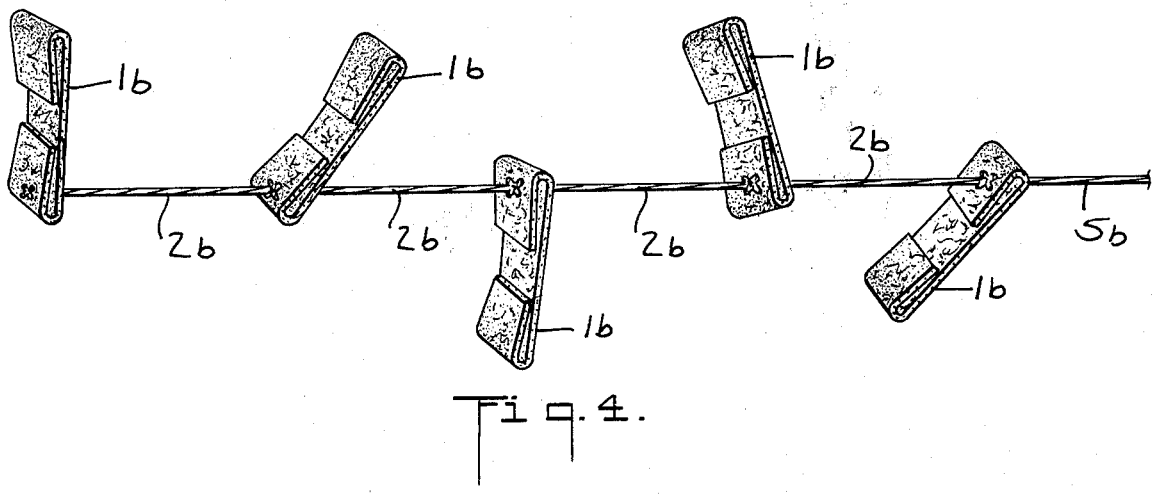

CATAMENIAL TAMPON

This is a continuation of application Ser. No. 271,453 filed July 13, 1972, and now abandoned.

The requirements of a suitable intravaginal catamenial device or tampon have been set forth in a number of U.S. patents relating to such products. These requirements have been delineated as stemming from considerations of physiology and anatomy. A representative sampling on the subject may be found in the following U.S. Patents:

Haesler Ser. No. 2,831,485 granted Apr. 27, 1958
Graham Ser. No. 2,858,831 granted Nov. 4, 1958
Piri Ser. No. 3,298,369 granted Jan. 17, 1967

The solution which Graham and Haesler attempted to provide was to devise a tampon which would be both sufficiently absorbent for its purposes and of such a physical configuration that it would better conform to the irregular internal shape of the vagina both at its initial placement therein and during its period of residence during which its main function of absorbence would be most efficiently carried out.

Graham devised several configurations, the main idea of which was to provide a tampon which would expand primarily in the length-wise direction. This was accomplished by forming the absorbent paper or cotton either in a spiral or in a series of absorbent discs or blocks including one embodiment in which the discs or blocks are attached one to the other along a string. The emphasis herein, however, is upon choosing such components that during expansion, upon becoming moistened, the fibers would expand primarily in a length-wise direction. The string in this case simply functioned to align the individual components so that this length-wise movement would be optimized.

Haesler directed his efforts to providing a tampon made of plurality of separate flexibly connected sections which in a sense might be described as independent pads, arranged in such a manner that they might individually adjust themselves in the vaginal passage for optimum disposition and absorbency.

Haesler's embodiments show two pad sections are arranged in a side-by-side relationship, attached loosely by a thread or string and which in effect become simply a pair of half-sized tampons divided along the lengthwise median.

Both of the prior art devices approach the problem on a basis of providing better conformation of the tampon to the vagina while attempting to diminish the unit bulk of the device. It is apparent that the devices of Graham and Haesler attempt to improve on those commonly used in this area of personal hygiene. It appears that such devices have not replaced those generally used possibly because they are not essentially different in their manner of functioning or in the results obtained.

The present invention represents an advance over the known attempts to produce a tampon which is readily comformable to the vaginal cavity, which is highly absorbent and which is less apt to present problems of soilage at the time of removal.

It is an object of the present invention to provide a catamenial tampon which will have a large surface to volume ratio.

It is further object of the present invention to provide a catamenial tampon made up of distinct portions spaced at such intervals along a thread that they needn't contact one another.

Further objects of this invention will be apparent from the following description and the several accompanying figures which are furnished by way of illustration and not by way of limitation.

FIG. 1 is a longitudinal cross-section through a tampon applicator combination.

FIGS. 2, 3 and 4 are embodiments of several arrangements of absorbent masses along a thread made in accordance with the requirements of the present invention.

The significant features of the tampon of the present invention are both the number of absorbent masses and their spacing along the thread. One end of the thread serves as a withdrawal means.

The absorbent masses 1 which are attached along thread 2 are of such cross-section and thickness that as shown in FIG. 1, they occupy a major portion of the storage tube 3 of an applicator when they are compressed therein. They may be deposited therefrom by the piston action of inner tube 4. Terminal portion 5 of thread 2 functions as a withdrawal means for removing the tampon from the vagina.

FIG. 2 shows a preferred embodiment of the absorbent masses 1 attached along thread 2 at such intervals that when fully expanded upon becoming saturated by menstrual fluids a clearance 6 remains between the absorbent masses 1. This permits withdrawal from the vagina by means of thread portion 5 of the relatively small absorbent masses 1 one at a time thereby avoiding loss of absorbed fluids due to squeezing. Thread 2 in this embodiment of the invention passes approximately through the center of each absorbent mass 1, shown as a disc in FIG. 2, the thread 2 being attached at a point to the adjacent surfaces of the discs between the clearance 6 in an "X" configuration as seen in FIG. 2. The same type attachment point is also shown in FIG. 4.

FIG. 3 shows the absorbent masses 1a with threads 2a individually attached between them at their alternate edges and having a terminal portion 5a to serve as a withdrawal means.

FIG. 4 shows another embodiment in which the absorbent masses 1b are in the shape of bows which are attached at one end of the bow and randomly arranged about the axis of thread 2b. The attachments are at such intervals that the required clearance between the absorbent masses 1b is maintained.

It is to be understood that the embodiments described above are merely illustrative. Other variations may be easily perceived which can be made by following the teachings of the present invention.

The absorbent masses may be made of any of the materials conventionally used for this purpose, such as absorbent cotton, cellulosic sheets or sponge or any highly absorbent, non-toxic material of the type generally known and used in the manufacture of tampons.

The specific shape of the absorbent masses is not a critical consideration in determining the functionality of the tampon but may be of any configuration which permits their being easily placed in an applicator and which, when fully expanded, are of such dimension with relation to the intervening length of thread are such that with the thread fully extended, the adjacent absorbent masses when flattened along the line of the thread are not sufficiently close together that their edges would touch. The absorbent masses may be in the shape of circles, squares, bows or any other regular or irregular shape so long as the completed article fulfills the requirements set forth above. The shape of the soft absorbent masses is not critical since upon becoming moistened they further soften and become rather shapeless.

A tampon made in accordance with the teachings of the present invention, when properly placed in the vagina, would not be subject to the faults usually associated with unitary tampons or those comprised of large absorbent masses. The tampon of the present invention comprising many individual units which may arrange themselves in a felted, random order form an efficient pad for collecting fluids and form a barrier to passage thereof.

A tampon made in accordance with the teaching of the present invention has the added advantage of being considerably less likely to cause soilage upon removal since the spacing between the absorbent units as determined by the length of thread between them insures the separate removal unit by unit without blockage due to the spacial relationship between them. The small cross-section further insures easy passage from the vagina as without loss of absorbed fluids from the individual units which make up the tampon.

A preferred embodiment was prepared as follows: Discs of absorbent, soft cotton felt about 1 inch in diameter were punched from a sheet having a thickness of about one-eighth inch. They were formed into groups of 2 or 3 and attached at distances of about 1.5 inches apart on a cotton thread. The individual discs were sewn together when the groups are formed in a shirred manner which further increased their surface area.

Five or six groups are attached along the thread as described above and enough thread is left over to provide a means for withdrawing the tampon after placement in the vagina. The groups are placed in an applicator in the conventional manner.

An applicator which may be used in conjunction with tampons of the present invention may be of a conventional type. One such device consists of two pieces of tubing the longer one being about 3 inches in length while the other is about 2.75 inches in length. Their cross-sections are such that the smaller, longer tube fits snugly inside the larger shorter tube. The tampon is packed into the piece of tubing having the larger diameter. The other piece of tubing is then partially inserted into the first one. It then may be operated as a piston which when activated pushes the packed tampon from the larger cylinder for deposition in the vagina.

Having described a preferred embodiment of my invention, it is obvious that there are many variations thereof which might be made which come within the scope of the following claims.

What is claimed is:

1. An intravaginal catamenial tampon which is suitable for insertion in the vagina by means of an applicator and which comprises a multiplicity of absorbent dimensional units attached to one another by means of a thread, each of said units having a front planar surface and a rear planar surface wherein the distance between said surfaces defines the width dimension of said unit, each surface of said units having an attachment point wherein said front planar surface attachment point of one unit is connected by said thread extending from said front planar surface attachment point to the rear planar surface attachment point of the next most adjacent unit, the size of the absorbent units and the length of said thread being such that the absorbent units cannot touch one another when the tampon is fully extended, and wherein said front planar surface of one of said units abuts said rear planar surface of the next adjacent unit when said tampon is assembled in said applicator.

2. A tampon as set forth in claim 1 wherein there are present at least four absorbent units having a greatest dimension of about 1 inch attached at intervals of about 1½ inches along a thread.

3. A tampon as set forth in claim 2 wherein the thread at one end of the assembly is sufficiently long to serve as a withdrawal means.

4. A tampon as set forth in claim 3 wherein said tampon is disposed within a two-piece applicator means from which it can be inserted into the vagina and deposited there.

5. A tampon as set forth in claim 1 wherein the planar surfaces are circular.

6. A tampon as set forth in claim 1 wherein the planar surfaces are rectangular.

* * * * *